US00PP09664P

United States Patent [19]

Olesen et al.

[11] Patent Number: Plant 9,664

[45] Date of Patent: Oct. 22, 1996

[54] SHRUB ROSE PLANT NAMED 'POULANS'

[75] Inventors: Pernille Olesen; Mogens Olesen, both of Fredensborg, Denmark

[73] Assignee: DeVor Nurseries, Inc., Watsonville, Calif.

[21] Appl. No.: 414,531

[22] Filed: Mar. 31, 1995

[51] Int. Cl.[6] ..... A01H 5/00

[52] U.S. Cl. ..... Plt./1

[58] Field of Search ..... Plt./1, 22, 26, Plt./27

*Primary Examiner*—Howard J. Locker

*Attorney, Agent, or Firm*—Christie, Parker & Hale, LLP

[57] ABSTRACT

A shrub rose variety producing cerise pink flowers.

1 Drawing Sheet

SUMMARY OF THE INVENTION

The present invention relates to a new and distinct shrub rose variety which was originated by our crossing as seed and pollen parents two unnamed and undistributed seedlings of our creation. The varietal denomination of this new rose is 'Poulans'.

Among the novel characteristics possessed by this new variety which distinguish it from its parents and all other varieties of which we are aware are its attractive cerise pink flowers borne on a bushy, vigorous plant.

Asexual reproduction by budding of the new variety as performed in Watsonville, Calif., shows that the foregoing and other distinguishing characteristics come true to form and are established and transmitted through succeeding propagations. Other known useful forms of asexual reproduction may be also employed.

BRIEF DESCRIPTION OF ILLUSTRATIONS

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—Unnamed, unpatented seedling.

*Pollen parent.*—Unnamed, unpatented seedling.

Class: Shrub.

The following is a detailed description of the new variety, from specimens grown outdoors in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

FLOWER

Blooming habit: Recurrent.

A. Bud:

(1) *Size.*—Small.

(2) *Form.*—Round with flat top.

(3) *Color.*—When sepals first divide, bud color is near 53C.

(4) *Sepals.*—Sepals unfurl and spread outwards, asymmetric with leaf–shaped tip, small prickles, about 0.1 cm to 0.125 cm long. Color: Near 138B.

(5) *Peduncle.*—Length: About 2 cm to about 6 cm. Aspect: Small prickles. Strength: Erect, sturdy. Color: Near 139C.

(6) *Bracts.*—About 2 to 6; near 138C, slender, elliptical with leaf pointed ends, about 2 cm to 6 cm below calyx.

B. Bloom:

(1) *Size.*—Average size when fully expanded — about 4.5 cm to about 5.5 cm.

(2) *Borne.*—Sprays of about 3 to 9 blooms.

(3) *Form.*—Rounded, petals ruffled at maturity open blooms reveal center.

(4) *Petalage.*—Number of petals under normal conditions — about 18 to 26.

(5) *Color.*—Outer petals — Top Surface: near 53A to 53B washing to near white at point of petal attachment; Undersurface: near 55B washing to near white at point of petal attachment. Inner Petals — Top Surface: near 53A; some petals with longitudinal near white streak. Undersurface: near 55B; some flowers display inner petals with visible longitudinal near white streak extending toward point of petal attachment. Base of petals (point of attachment) — Near 155D. General tonality from a distance: Cerise pink.

(6) *Flower clusters.*—Some flower clusters include a terminal pink flower near 56A with outer petal undersurface near 56C to 56D. This terminal pink flower amid other flowers of generall red coloration in a spray is typical of this variety. It is not an indication of lack of stability but rather a typical characteristic. General tonality from a distance: Cerise pink.

(7) *Color change.*—As bloom ages: Coloration becomes more intense; near 45A. Petal top surface: Intense red with white at center. Petal undersurface: Intense red with white at center General tonality at a distance: Cerise pink.

C. Petals:

(1) *Texture.*—Medium, smooth.

(2) *Appearance.*—Inside matte and outside slightly velvety.

(3) *Form.*—Wedge-shaped with apex emarginated.

(4) *Arrangement.*—Imbricated.

(5) *Petaloids.*—None.

(6) *Fragrance.*—None.

(7) *Lasting quality.*—Not suitable for cut flower, several days on plant.
(8 ) *Persistence.*—Petals drop off cleanly.

REPRODUCTIVE ORGANS

A. Stamens:
(1) *Arrangement.*—Irregularly arranged around styles.
(2) *Stamens.*—Near 22A.
(3) *Anthers.*—Color near 22B.
(4) *Filaments.*—Near 14D.
(5) *Pollen.*—Color — near 22A.
B. Pistils:
(1) *Styles.*—Bunched, with even length.
(2) *Stigmas.*—Color near 160A.
C. Characteristics of hips: Not observed.

PLANT

A. Form: Mounds.
Growth: Very vigorous; about 91 cm to about 122 cm in height and width at first season.
C. Foliage: Compound 3, 5 or 7 leaflets.
(1) *Size.*—Medium.
(2) *Quantity.*—Abundant.
(3) *Color.*—New foliage — upper side near 137A; underside near 137C; mature foliage — upper side near 137A, underside near 137C.
(4) *Shape.*—Elliptic.
(5) *Texture.*—Upper side slightly leathery, smooth; underside matte.
(6) *Edge.*—Serrate.
(7) *Serration.*—Denticulate.
(8) *Leaf stem.*—Color — medium green.
(9) *Stipules.*—Adnate with hairy extensions, glandular.
(10) *Rachis.*—Many prickles.
(11) *Petioles.*—Top near 137B, underside near 137D.
(12) *Auricle.*—Slender extensions with glandular tips.
(13) *Resistance to disease.*—Very resistant to blackspot, meldew and rust.
D. Wood:
(1) *New wood.*—Color near 138A, bark smooth.
(2) *Old wood.*—Color near 137B, bark smooth.
F. Thorns:
(1) *Thorns.*—Quantity On means stalk, average; laterals from stalk, many. Form: thin, curved downward. Length: Medium. Color: Near 161B. Position: Irregular.
(2) *Prickles.*—Profuse.
G. Winter hardiness: Winter hardy in Denmark and Watsonville, Calif.

I claim:

1. A new and distinct shrub rose plant variety, substantially as shown and described.

* * * * *

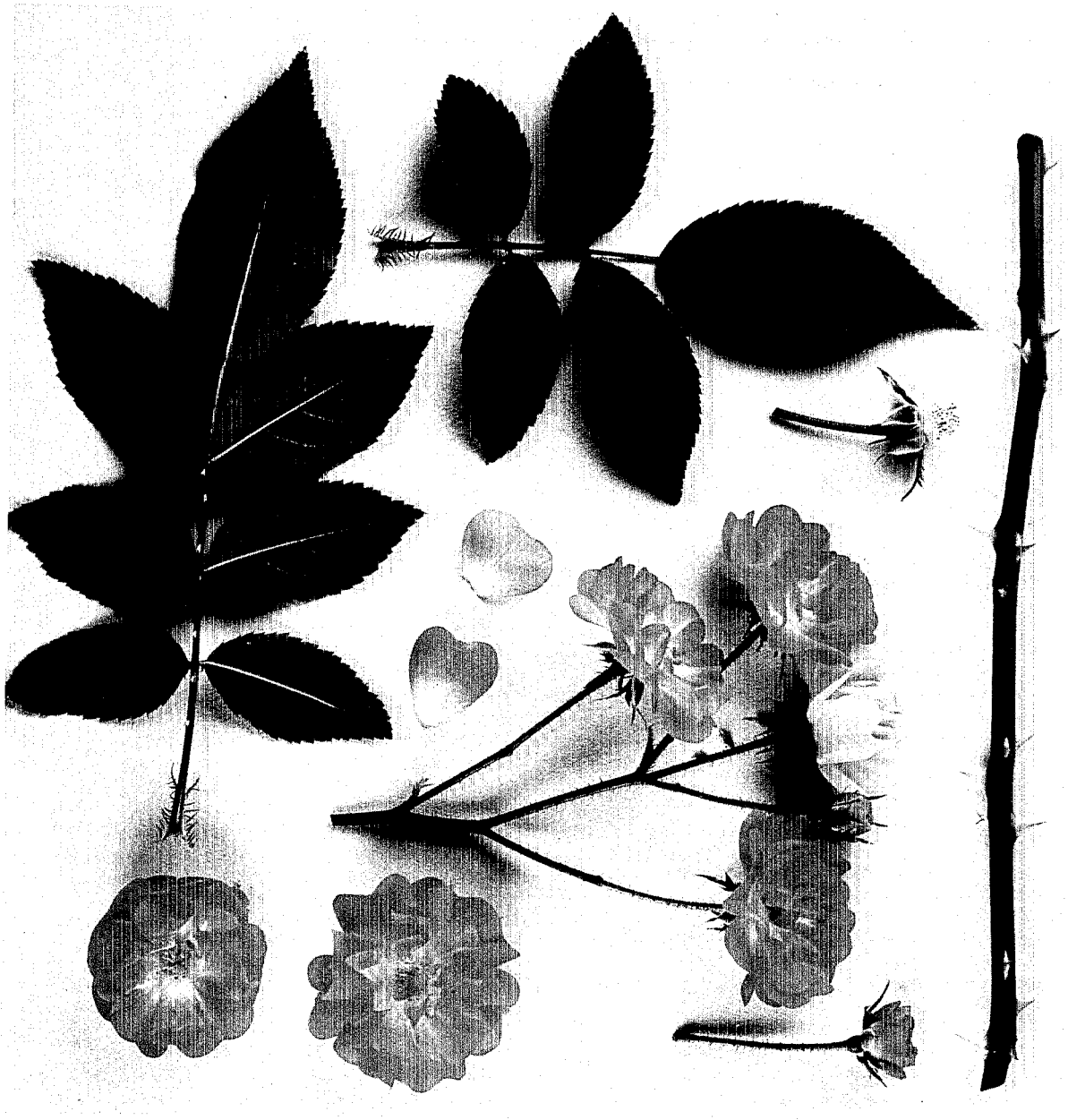

UNITED STATES PATENT AND TRADEMARK OFFICE

CERTIFICATE OF CORRECTION

PATENT NO. : Plant 9,664
DATED : October 22, 1996
INVENTOR(S) : Pernille Olesen; Mogens Olesen It is certified that error appears in the above-indentified patent and that said Letters Patent is hereby corrected as shown below:

Column 1, line 20, change "ILLUSTRATIONS" to -- ILLUSTRATION --.
Column 2, line 23, before "petals" insert -- inner --.
Column 2, line 42, change "center General" to -- center. General --.
Column 4, line 12, change "meldew" to -- mildew --.
Column 4, line 17, change "Quantity On means" to -- Quantity: On main --.

Signed and Sealed this

Eleventh Day of March, 1997

*Attest:*

*Attesting Officer*

BRUCE LEHMAN

*Commissioner of Patents and Trademarks*